(12) United States Patent
Gallant et al.

(10) Patent No.: US 6,725,483 B2
(45) Date of Patent: Apr. 27, 2004

(54) APPARATUS AND METHOD FOR UPGRADING A HOSPITAL ROOM

(75) Inventors: Dennis J. Gallant, Harrison, OH (US); John W. Ruehl, Shelbyville, IN (US); John C. Gray, Great Falls, MO (US); Edward W. Catton, New Palestine, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 09/105,255

(22) Filed: Jun. 26, 1998

(65) Prior Publication Data

US 2002/0152555 A1 Oct. 24, 2002

Related U.S. Application Data

(63) Continuation-in-part of application No. 08/792,881, filed on Jan. 31, 1997, now Pat. No. 5,966,760.

(51) Int. Cl.7 .............................. A61M 16/00
(52) U.S. Cl. ............................ 5/658; 5/503.1
(58) Field of Search ............... 5/600, 658, 503.1; 280/47.34, 47.371, 79.3, 35, 47.35, 47.17, 47.21, 47.22, 47.315, 1.167

(56) References Cited

U.S. PATENT DOCUMENTS

| 3,660,591 | A |   | 5/1972 | Schultz et al. |
|---|---|---|---|---|
| D226,353 | S |   | 2/1973 | Schultz et al. |
| 3,769,502 | A |   | 10/1973 | Schultz et al. |
| 4,003,584 | A |   | 1/1977 | Zelli |
| 4,178,005 | A | * | 12/1979 | Kent, Jr. ............... 280/43.18 |
| D261,804 | S |   | 11/1981 | Foster et al. |
| 4,417,648 | A |   | 11/1983 | Anderson et al. |
| 4,523,683 | A |   | 6/1985 | Fullenkamp et al. |
| 4,628,553 | A |   | 12/1986 | Buttitta et al. |
| 4,646,211 | A |   | 2/1987 | Gallant et al. |
| 4,662,524 | A |   | 5/1987 | Fullenkamp et al. |
| 4,768,241 | A | * | 9/1988 | Beney ....................... 5/658 X |
| 4,790,610 | A |   | 12/1988 | Welch et al. |
| 4,821,470 | A |   | 4/1989 | Kappers et al. |
| 4,875,696 | A | * | 10/1989 | Welch et al. ......... 280/47.364 |
| 4,993,683 | A | * | 2/1991 | Kreuzer ..................... 248/639 |
| 5,026,017 | A |   | 6/1991 | Kreuzer |
| 5,040,765 | A |   | 8/1991 | Schonfelder |
| 5,060,425 | A |   | 10/1991 | Kappers et al. |
| 5,072,906 | A |   | 12/1991 | Foster |
| 5,077,843 | A |   | 1/1992 | Foster et al. |
| 5,107,636 | A |   | 4/1992 | Schindele et al. |
| 5,108,064 | A |   | 4/1992 | Kreuzer |
| 5,117,521 | A |   | 6/1992 | Foster et al. |
| 5,135,191 | A | * | 8/1992 | Schmuhl ................... 5/658 X |
| 5,186,337 | A |   | 2/1993 | Foster et al. |

(List continued on next page.)

FOREIGN PATENT DOCUMENTS

| CA | 2 018 094 | 12/1990 |
|---|---|---|
| DE | 298 05 019 | 6/1998 |
| EP | 0 400 407 | 12/1990 |
| FR | 2 669 199 | 11/1990 |
| WO | 98/33419 | 8/1998 |

OTHER PUBLICATIONS

CABG Cart, "Lettuce Trade Your Spaghetti For The CABG Cart", date unknown, 5 pages.
Hill–Rom, Inc., "Stabilet From Hill–Rom", 1992, 6 pages.

Primary Examiner—Teri Pham Luu
Assistant Examiner—Fredrick Conley
(74) Attorney, Agent, or Firm—Barnes & Thornburg

(57) ABSTRACT

An overhead support for receiving medical appliances comprises an extension arm and appliance receiving means and is modified for receiving various chassis-mounted appliances on said appliance receiving means. To this end the appliance receiving means is level-adjustable such that it receives a medical appliance carried on a chassis by grabbing the chassis from below.

32 Claims, 8 Drawing Sheets

U.S. PATENT DOCUMENTS

| | | |
|---|---|---|
| 5,284,255 A | 2/1994 | Foster et al. |
| 5,297,820 A | 3/1994 | Martin |
| 5,299,338 A | 4/1994 | Foster |
| 5,306,109 A * | 4/1994 | Kreuzer et al. ............. 414/343 |
| 5,323,565 A | 6/1994 | Kappers et al. |
| D349,668 S | 8/1994 | Mathews et al. |
| 5,335,651 A | 8/1994 | Foster et al. |
| 5,337,845 A | 8/1994 | Foster et al. |
| 5,344,169 A | 9/1994 | Pryor et al. |
| 5,348,324 A | 9/1994 | Trotta |
| 5,370,111 A | 12/1994 | Reeder et al. |
| 5,377,371 A | 1/1995 | Foster |
| 5,398,359 A | 3/1995 | Foster |
| 5,455,975 A | 10/1995 | Foster |
| 5,457,831 A | 10/1995 | Foster et al. |
| 5,490,652 A | 2/1996 | Martin |
| 5,497,766 A | 3/1996 | Foster et al. |
| 5,527,125 A | 6/1996 | Kreuzer et al. |
| 5,562,091 A | 10/1996 | Foster et al. |
| 5,598,869 A | 2/1997 | Nelson |
| 5,618,090 A | 4/1997 | Montague et al. |
| 5,645,538 A * | 7/1997 | Richmond .................. 604/256 |
| 5,711,340 A | 1/1998 | Gusky et al. |
| 5,784,732 A * | 7/1998 | Vail .............................. 5/430 |
| 5,898,961 A * | 5/1999 | Ambach et al. ............ 5/658 X |

* cited by examiner

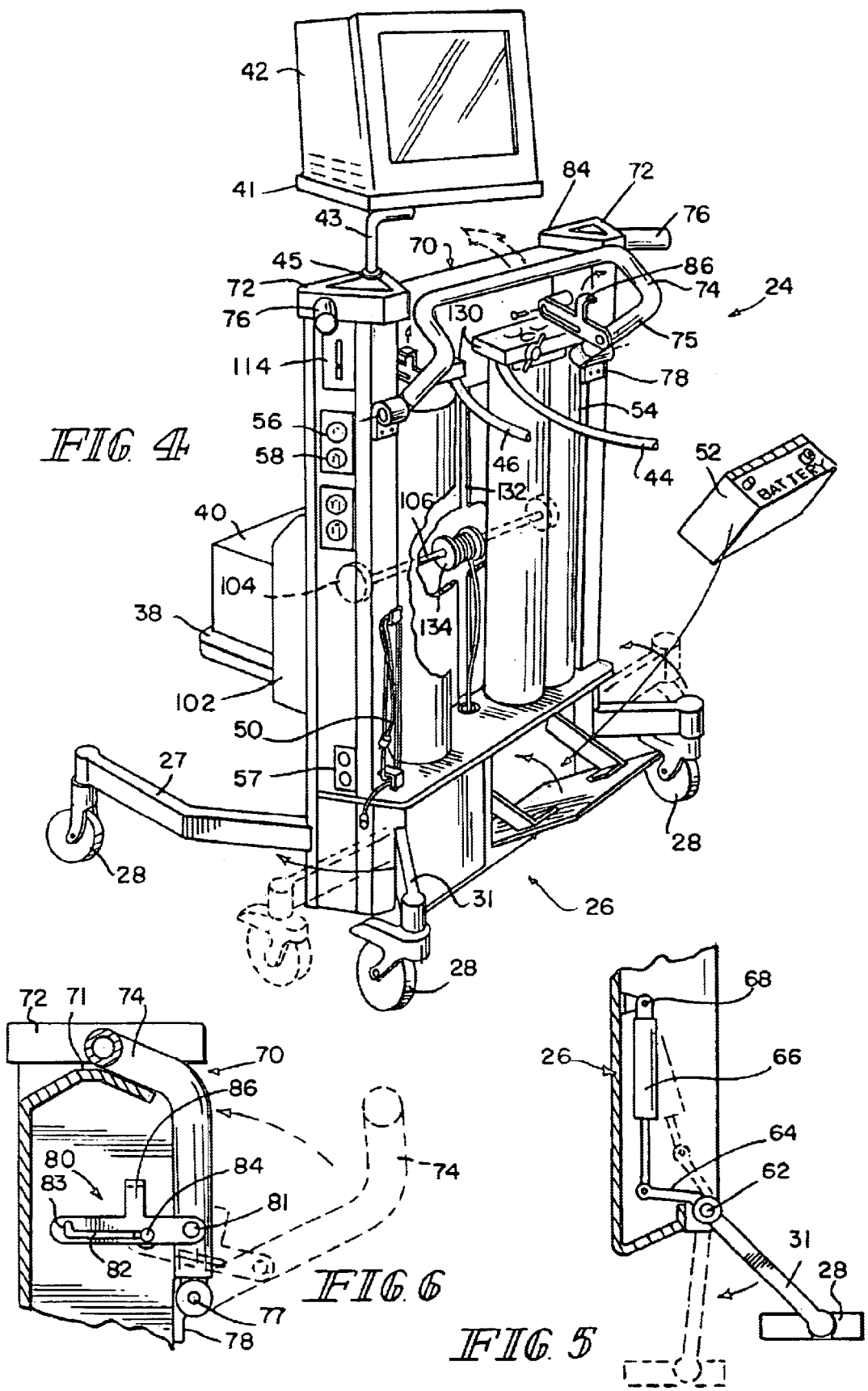

APPARATUS AND METHOD FOR UPGRADING A HOSPITAL ROOM

CROSS REFERENCE

This is a continuation in-part of U.S. patent application Ser. No. 08/792,881, filed Jan. 31, 1997, now U.S. Pat. No. 5,966,760 which is incorporated herein by reference.

BACKGROUND AND SUMMARY OF THE INVENTION

The present invention relates to an apparatus and method to facilitate upgrading of a standard, general care hospital room to a critical room. More particularly, the present invention relates to an improved apparatus and method for providing seamless critical care services to a patient in a hospital room and during transport of the patient within the hospital.

Recent trends have caused cost reducing pressures on hospitals. These cost pressures have driven traditional in-patient services to less expensive out-patient and home care settings. Therefore, hospitals tend to have smaller in-patient populations. Future in-patient populations are likely to be older and sicker patients with multiple complications. The population of intermediate care patients is also likely to increase while the med-surg hospital population is decreasing over time. Therefore, the in-patient hospital population has a higher level of acuity.

Hospitals will likely have fewer beds in the future. Reconstruction of hospital rooms for critical care services is very expensive. Typically, existing structures must be torn out and rebuilt with critical care capabilities.

It is known to provide a pivoting power column built within the room to provide life support services for critical care patients. These pivoting power columns, however, are not transportable and must be built within the particular hospital room. See, for example, U.S. Pat. Nos. 5,398,359; 5,377,371; 5,284,255; 5,186,337; and 5,072,906.

Several problems face hospital administrators and planners. Facilities within inflexible architectural systems restrict the ability of institutions to upgrade services quickly and inexpensively. In addition, the process of transporting critical care patients creates adverse conditions and risks for staff and patients due to the inability to easily move and maintain power for the ventilator and/or IV pumps and transport monitor.

In order to adapt to changes for fewer but more acute patients, hospitals need the option for more responsive architectural systems and patient rooms that can be upgraded to critical care or downgraded to med-surg quickly and inexpensively. In order to accomplish these needs and to reduce the number of staff and time required to transport a critical care patient, hospitals need a mobile equipment system that can support and provide power, medical gases, and a communication interface to a ventilator, IV pumps and/or a patient monitor. The system must consume minimum space within a patient room, be able to fit substantially within the footprint of the patient bed during transport, and organize and manage lines connected to the patient.

The apparatus of the present invention provides a mobile care cart which mates with an architectural headwall or pivoting power column that allows a hospital to create a "general care" patient room that can be upgraded quickly and efficiently to a critical care room "upon demand" without remodeling the room. The apparatus of the present invention allows a general care "flexible" headwall or pivoting power column with services that can be upgraded or downgraded easily. In addition, the care cart supports critical care devices such as the ventilator, pumps, etc. at the bedside. The care cart can be coupled to the patient bed for manually transporting the patient. During the transport the mobile care cart provides uninterrupted power for critical care devices.

The care cart provides a platform for mounting primary critical care equipment. A ventilator is mounted on a movable, power assisted and adjustable shelf so that the ventilator can be positioned in an elevated position when the mobile care cart is used in the hospital room. When it is desired to transport the critically ill patient within the hospital, the mobile care cart is disconnected from the headwall or power column and connected to an end of the patient's hospital bed. An on-board power supply on the care cart supports the ventilator during transport. Pivoting IV poles on the care cart can swing into a nested position adjacent the bed for transport. During transport, the equipment shelf is lowered to a position below the bed.

While the critical care patient remains in the hospital room, the mobile care cart integrates with and is nested with the headwall or power column. The care cart is connected to the main power supply of the room and the ventilator is connected to oxygen or air supplies in the headwall or power column in a conventional manner.

The mobile care cart of the present invention includes a base, a patient treating apparatus on the cart and a handle. The handle on the cart is pivotally coupled to pivot between a stored position and extended position. The handle is U-shaped and pivotally connected at its ends. Preferably, the handle includes extensions extending from the end of the U-shape and transverse to the plane of the U. The extension is pivotally mounted to the handle to the cart. The cart includes a recess in which the handle lies in the stored position. A stop connects the handle to the cart and limits the extended position. The stop, preferably, is a bracket having a first elongated slide and a pin riding in the slot. The bracket includes a second slot extending transverse to the first slot in which the pin rides to latch the handle in the extended position. This bracket is considered a second latch. A tab extends from the bracket to facilitate lifting of the bracket to move the pin from a second slot to the first slot for releasing the second latch.

A mobile cart according to the present invention has a base with wheels. At least one leg is pivotally mounted adjacent at one of its ends to the base and one of the wheels is mounted on the leg adjacent the second end of the leg. A driver coupled to the arm maintains the leg, in a first position. A spring biases the leg to the first position. The leg includes a shaft pivotally mounted to the base and the driver is coupled to the shaft. The driver is in the housing of the base. Preferably, the pivotal leg with the driver are provided as a pair of back legs adjacent the back of the base. A pair of front legs are fixedly mounted adjacent the front of the base at a first end and have wheels mounted at the second end of the front legs.

While the first position of the back extends backwards from the back of the base, the second position is substantially coplanar with the back of the base. The coplanar position allows the back of the base to be as close as possible to an object in the room or elevator in which the bed is located, for example, the wall. It also increases the stability of the cart when it is not connected to the bed so as to meet the requirements that will not turn over at 10° of tilt. In the first position where the back legs are not coplanar to the base, they decrease the transverse profile of the cart when attached to the bed. This is not detrimental since the bed has stability against the 10° tilt and also allows the cart and combination of the bed to get through doorways and into elevators.

The mobile cart of the present invention can be part of a power column which has electrical outlets, fluid ports and other patient treating accessories. The power column would have upper and lower separable sections. An arm would mount the upper section to the room. The lower section would be the mobile care cart which would include wheels and patient treating accessories on the lower section. The lower section of the mobile cart would provide patient treatment when the bed and the lower section are moved relative to the upper section. The upper section would include a recess in which a portion of the lower section would nest. Also, the lower section includes a recess for a portion of the upper section to nest. The lower section would move with the upper section independent of the bed when the lower section is not coupled to the bed by a latch. A second latch, or a press fit would connect the upper and lower section of the power column. The first and second sections separate when the lower section is coupled to the bed and moves the bed relative to the upper section to overcome the press fit. IV racks and patient monitors may be coupled to the lower section.

The mobile care cart includes a support coupled to the cart movable relative to the base between an elevated and a lowered position. Patient treating accessories are provided on the movable support. The support includes a port to be connected to one of the patient treating accessories movable with the support and a line connecting the port to the source on the cart. A take-up-reel on the cart engages the line to change the length of the line with the movement of the support. A drive couples the movement of the support to the spool. Preferably, the take-up-reel is on the movable support and engages the line to change the length of the line with the movement of the support. The line can be an electrical cord connected to a source of electricity on the cart or the line could be a tube connecting a fluid source on the court. This structure minimizes the entanglement damage and disconnection of the line during transport of the cart as well as adjustment of the support.

Other objects, advantages and novel features of the present invention will become apparent from the following detailed description of the invention when considered in conjunction with the accompanying drawings.

BRIEF DESCRIPTION OF THE DRAWINGS

FIG. 4 is a rear perspective of the mobile care cart illustrating the two positions of the rear wheels and a partial cut-away, without IV poles.

FIG. 5 is a partial cut-away illustrating the driver and the two positions of the rear wheels according to the principles of the present invention.

FIG. 6 is a partial cut-away view illustrating the two positions of the rear handle.

DETAILED DESCRIPTION OF THE DRAWINGS

Figure 1:
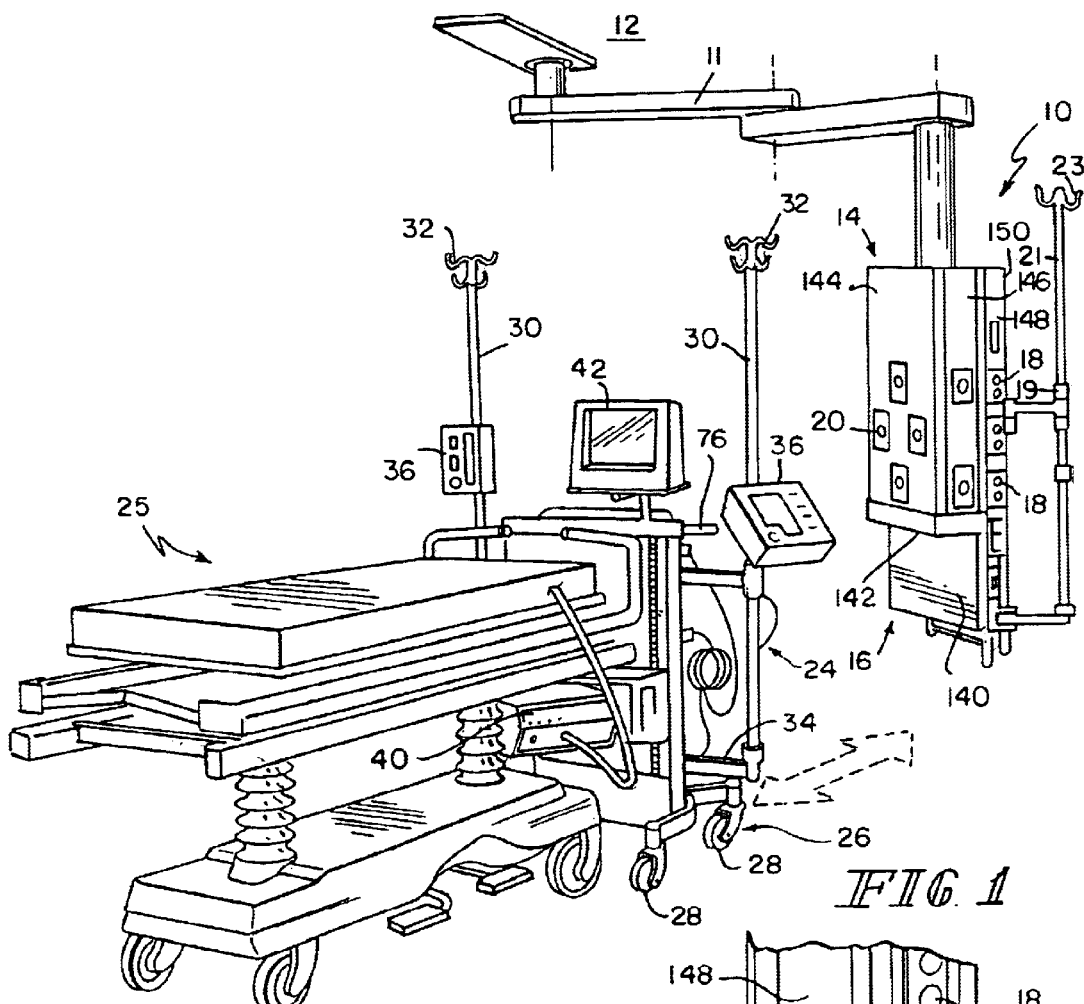
FIG. 1 is a perspective view of a mobile care cart attached to a bed and a pivotally mounted power column according to the principles of the present invention.
Figure 2:
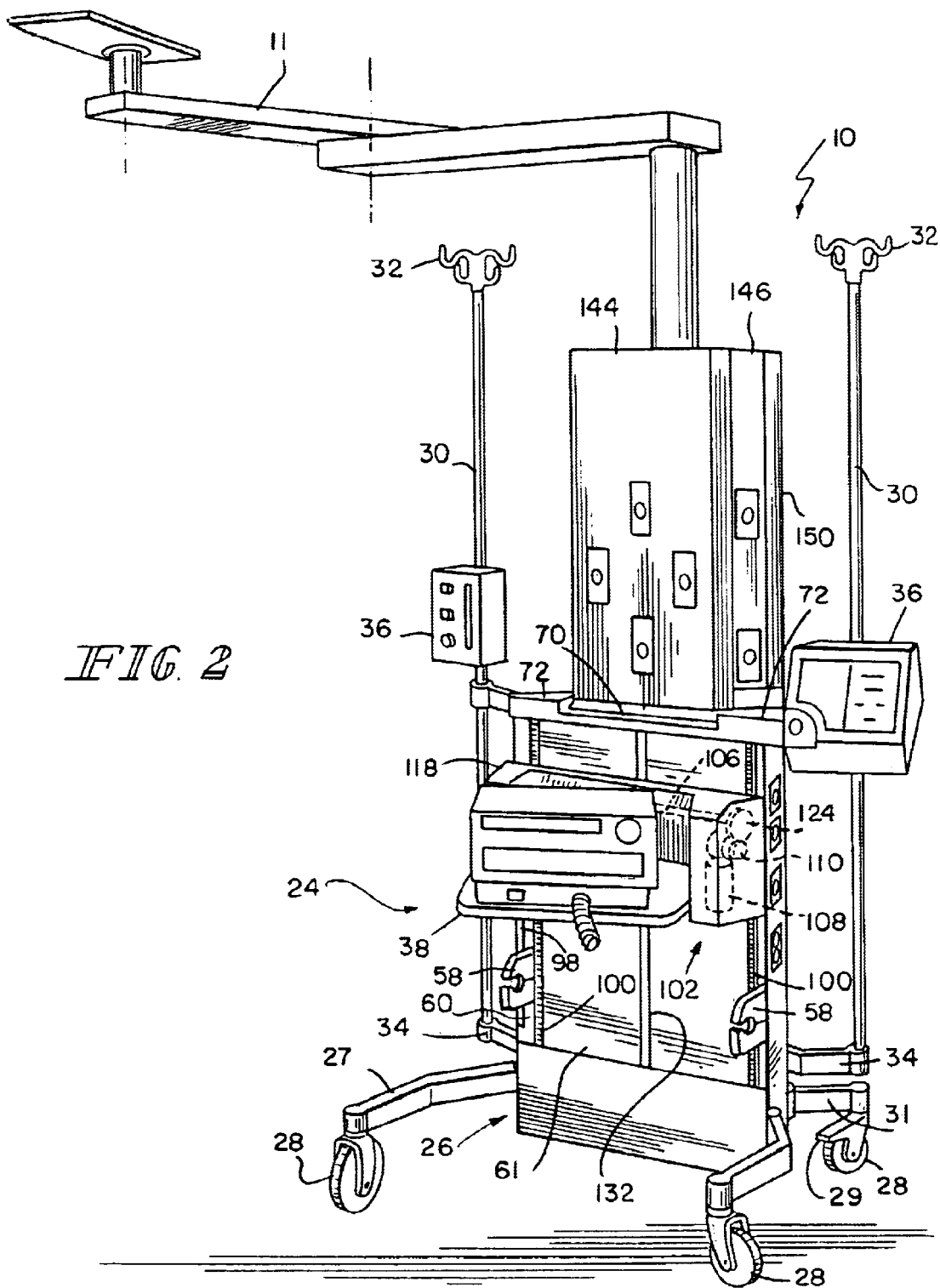
FIG. 2 is a perspective view of the care cart nested with the pivotal power column incorporating the principles of the present invention.

Referring now to the drawings, FIGS. 1 and 2 illustrate the system and structural components of the present invention for providing a hospital room capable of upgrading services quickly and inexpensively. A headwall or power column 10 is pivotally mounted on a ceiling 12 of a hospital room by arms 11. The power column 10 includes an elongated body section 14 and a bed locator section 16. The power column 10 includes outlets 18 for electrical power and outlets 20 for oxygen, air, and vacuum. A pivoting IV pole 21 with a hook 23 for hanging IV bags is mounted on body section 14. A pivotal lock 19 on the IV pole allows rotation of the top of the pole relative to the bottom of the pole. The lock 19 may be a detent or friction lock. The power column 10 can be used by itself in the room to provide for general care and support and for med-surg patients, for example.

When it is desired to upgrade the hospital room into a critical care room, a care cart 24 is moved into the room adjacent a bed 25. The care cart 24 includes a base 26 having casters 28. The front casters are on legs 27 fixed to the base 26. The rear casters 28 are lockable by separate brakes 29 and are on legs 31 pivotally connected to the base 26. A pair of IV poles 30 are pivotally mounted on the base 26 by arms 34. A pivotal lock equivalent to lock 19 may be provided. This allows the IV poles 30 to be pivoted from various use positions adjacent the side or front of the care cart 10 to behind the care cart. Preferably, the IV poles 30 are positioned between the rear wheels 28 during transport. This provides protection of the pump during transport and minimizes the width. The poles 30 include hooks 32 for hanging IV bags. IV pumps 36 may also be mounted on the poles 30.

Care cart 24 also includes an equipment support shelf 38 for supporting a full end ventilator 40 or other critical care equipment. Ventilator 40 may be secured to the shelf 38 by latching brackets (not shown). The support shelf 38 is movable from an elevated, in-room position illustrated in FIGS. 1 and 2 to a lowered transport position illustrated in FIG. 4 as discussed in detail below. The movable equipment shelf 38 therefore facilitates transport of the ventilator 40 with the care cart 24 during movement of the critical care patient.

A transport monitor 42 can also be mounted to care cart 24 during transport as illustrated in FIGS. 1 and 4. The transport monitor 42 includes or rests on a shelf 41. A post 43 extends from the bottom of shelf 41 and is pivotally connected to the care cart 24 in hole 45.

Figure 13:
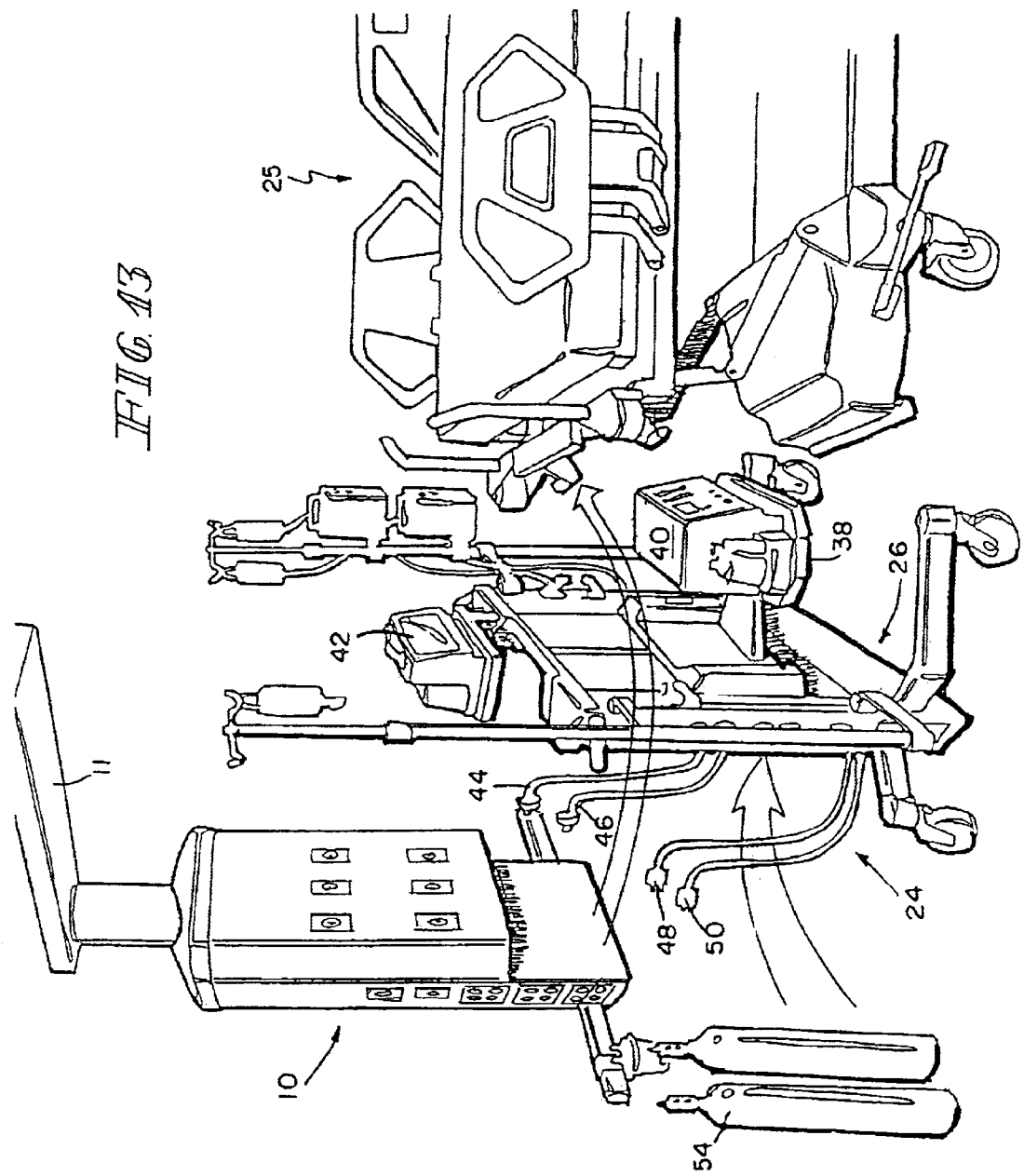
FIG. 13 is a perspective view of a power column, care cart and bed in a transition state.

The mobile care cart 24 further includes an air hose or line 44, an oxygen hose or line 46, and a standard power cord or line 50 as shown in FIG. 4. A separate power cord 48 to charge the battery may be provided as shown in FIG. 13. Care cart 24 also includes a transport battery 52 to operate equipment during transport of the critical care patient. The battery 52 provides power for the ventilator 40 and other critical care equipment during transport. The IV pumps 36 and transport monitor 42 each typically have an internal power supply. The battery 52 is recharged when the care cart 24 is plugged into the power column outlets 18. Gas tanks 54 are also provided on care cart 24.

A vacuum pump for providing integral suction can be provided on the cart 24. A vacuum level adjustment controller, gauge, and connector are also included on the care cart 24 to provide suction on the cart 24 during transport.

Care cart 24 includes an upper series of electrical outlets 56 which are powered only when the care cart is plugged into the power column outlet 18. As shown in FIG. 4, the care cart 24 includes separate power outlets 57 are automatically powered by the battery 52 when the care cart 24 is unplugged from the power column outlets 18. Therefore, the equipment requiring power during transport must be plugged into the designated lower outlets 57 for an uninterrupted power supply from the battery 52.

In order to upgrade the hospital room to a critical care room, care cart 24 is moved into the position illustrated in FIG. 2. Power cord 50 is plugged into the outlet 18 of power column 10. Air and oxygen lines 44 and 46 are connected to the gas outlets 20. Preferably, the connection of the power cord or line 50 and gas lines 44 and 46 are to outlets on the rear of the power column 10. In the position of FIG. 2, the battery 52 is recharged and air and oxygen tanks 54 are shut off to keep the tank supplies from being depleted. Also as illustrated in FIG. 2, the care cart 24 is configured to nest with the locator section 16 of power column 10. Therefore, the hospital room can be upgraded to a critical care room without reconstruction.

The care cart 24 is also used to transport the critical care patient within the hospital. For example, the care cart 24 is coupled to the hospital bed 25 as discussed below. Using the care cart 24 to transport the patient provides seamless care for the patient during transport to the radiology department or other diagnostic testing facility within the hospital.

When it is desired to transport the critical care patient, oxygen and air tanks 54 are loaded on to the care cart 24 as illustrated in FIGS. 4 and 13. Transport monitor 42 is also attached to the care cart 24. Prior to transport, valves on the oxygen and air tanks are manually opened to supply gas through a manifold 130 to the ventilator 40. The gas lines 44 and 46 and power cord 50 of care cart 24 are then disconnected from power column 10. Battery 52 on the care cart 24 automatically switch on to support the ventilator 40 when the power cord and 50 are disconnected.

For transport, the equipment shelf 38 is lowered to the transport position illustrated in FIGS. 1, 4 and 13 and the bed is raised. For visualization of equipment, such as a ventilator 40, the equipment shelf 38 supporting the equipment 40 can be rotated if desired. The transport position of the equipment shelf 38 allows the equipment, such as a ventilator 40 to be transported under the sleep surface frame of the bed and within existing dimensions of the bed 25 as shown in FIG. 1. This allows the equipment to be transported with the bed and still fit within existing elevators in the hospital.

Next, the care cart 24 is coupled to the bed using the latch mechanisms 58 shown in FIG. 2. The latch mechanism 58 on the care cart 24 is coupled to pins (not shown) attached to frame of the bed 25. The latch mechanism 58 rides in slots 60 in the front of face 61 of the care cart 24 and its height is adjustable. It is understood that the care cart 24 can be coupled to either a head end or foot end of the bed 25.

The IV lines and vent circuits do not need to be disconnected from the patient prior to transport. The IV pumps 36 and ventilator 40 also do not need to be handled. This method maintains seamless, uninterrupted functioning of the life support to the patient.

The bed 25 and the care cart 24 are then transported as a unit as illustrated in FIG. 1. A caregiver can use a rear push-handle 74 to guide the care cart 24 and bed 25 from the rear or either side handle 76 to guide from the side. During transport, the IV pumps 36 and monitor 42 operates on their own internal batteries. The equipment without internal batteries operate on the battery 52 of care cart 24 through designated outlets 57. Battery 52 provides battery power for the transport procedure.

At the destination, the care cart 24 is coupled to medical gas and wall or tower electrical outlets to prevent depleting of the on-board gas tank 54 supplies and battery 52. A cross over valve allows the cart to be connected to the medical gas supply for a limited period of time with negligible leakage of gas from the tanks 54. The patient can then be transferred to a scanning table. The bed 25 can be removed from the care cart 24 and taken from the room. Therefore, the care cart 24 can remain adjacent the scanning table to continue to provide life support for the patient.

The original transport procedures are followed for the return trip to the room. Upon returning the patient to the room, the care cart 24 is plugged into the electrical outlets 18 and gas outlets 20 of the power column 10 as discussed above. The transport monitor 42 is removed. The care cart 24 is separated from the bed to permit the ventilator 40 on the shelf 38 to be moved to the elevated position of FIG. 2. The equipment shelf 38 is then rotated and reoriented so that the displays on the critical care equipment 40 are facing outwardly into the room. A care cart 24 is then moved adjacent the hospital bed 25 into the nested position with the power column 10 of FIG. 2 to resume in-room critical care services. It is understood that the care cart 24 can be positioned in any orientation at the head end of bed 25.

The front legs 27 of base 26 are long enough to pass beyond casters of the hospital bed base and are separated wide enough to encompass the bed casters and still be within the foot print of the bed. For example, the front legs 27 extend at least 15.5 inches from the face 61 of the care cart 24. The center to center separation of the pivot point of the casters on the front legs 27 is approximately 37.5 inches for 5 inch casters 28.

The rear legs 31 include a shaft 62 pivotally mounted to base 26 as shown in FIG. 5. A linkage 64 connects a driver 66 to shaft 62. The driver 66 is pivotally connected to the base at 68 and may be a mechanical or fluid spring. It maintains the rear leg 28 in a first position extending backward from the cart 24 and preferably, within the width of a bed. To minimize the depth of the base 26, the legs 31 can pivot to a second position substantially coplanar with the back of the base 26 (shown in phantom). This may be accomplished by backing the base into a wall, for example, a wall of a room or an elevator. The side handle 76 allows positioning of the bed and cart in an elevator and to press the rear wheel legs 31 against a wall.

Figure 7:
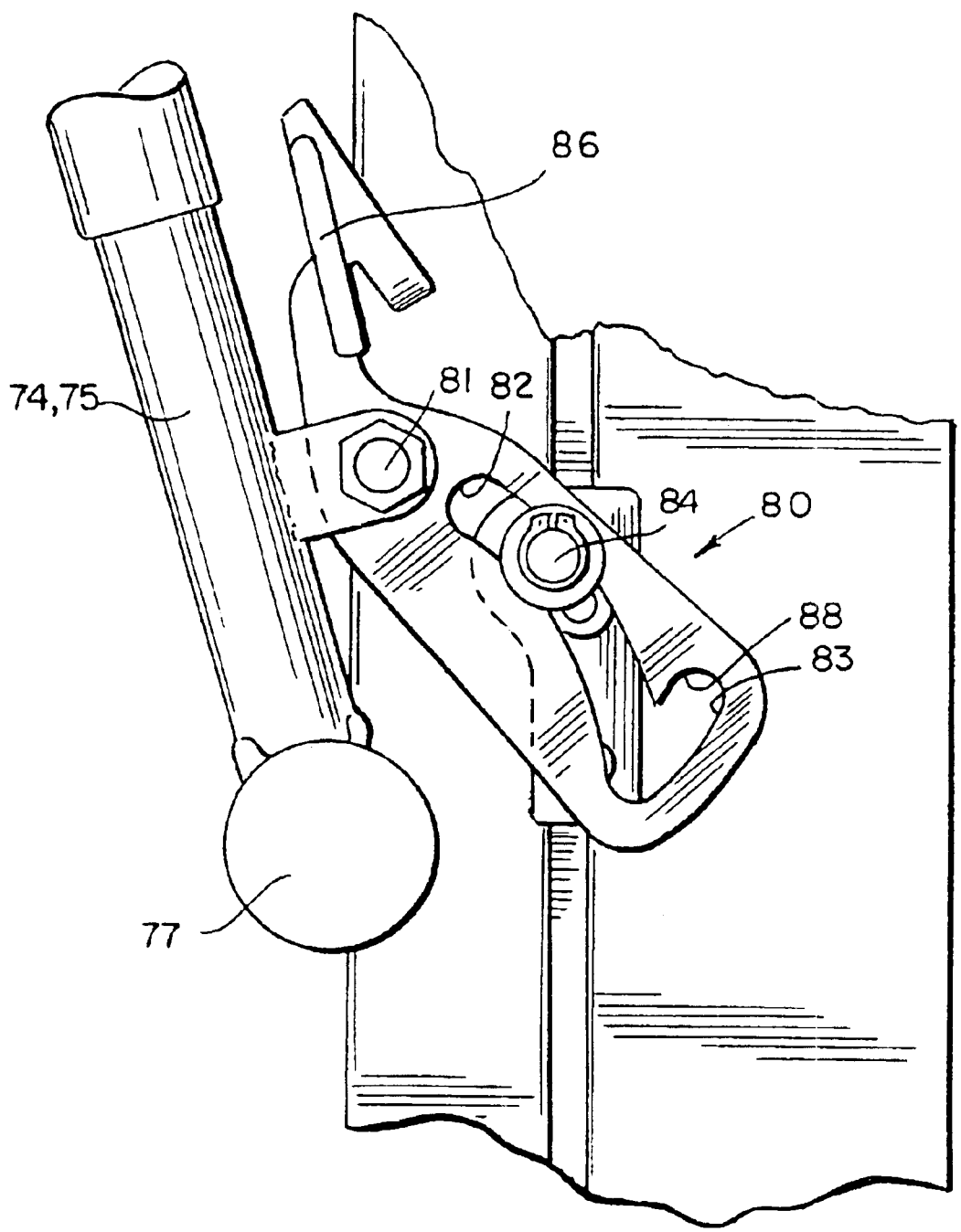
FIG. 7 is a side view of another embodiment of a stop structure for the rear handle.

The rear push handle 74 is pivotally connected to the rear of the care cart 24 by brackets 78 and has a stored position as illustrated in FIG. 7 and an extended position illustrated in FIG. 4 and in phantom in FIG. 6. In the stored position, the handle 74 lies in the recess 70 between the land 72 and on a top wall 71 of the care cart. The push handle 74 is U-shaped and includes extensions 75 extending from the ends of the U-shape and transverse to the plane of U-shape. The extensions 75 have ends 77 pivotally mounting the push handle 74 to the cart at bracket 78. Preferably, the handle 74 is coated with a non-slip grip material.

A stop or latch bracket 80 is connected between the handle 74 and a side wall of the care cart 24. The stop or latch bracket 80 is pivotally connected at 81 to the handle 74 on extension 75 and includes a first elongated slot 82 and a second elongated slot 83 transverse the first elongated slot 82. A pin is 84 mounted to the side wall of the care cart and rides in the elongated slots 82 and 83. The ends of the first elongated slot 82 forms a stop for the extended and stored position of the handle 74. The second elongated slot 83 forms a latch to latch the handle 74 in its extended position when the pin 84 rides up into elongated slot 83. A tab 86 extends from the stop or latch bracket 80 to reposition the pin 84 from the elongated slot 83 down into elongated slot 82. Thus, the handle 74 can then be raised to its stored position along slot 82.

FIG. 7 shows another embodiment of the stop or latch bracket 80. The elongated slot 82 is curved instead of linear as it is in FIG. 6. Also, a lobe 88 has been added to the terminus of slot 83 extending generally transverse to the slot 83. The stop or latch bracket 80 is mounted to the front face of the extension 75 of the handle 74 in FIG. 7 versus the side as shown in FIG. 6. The tab 86 extends from the bracket past the pivot point 81 in FIG. 7 where it is within the body of the stop or latch bracket and adjacent the elongated slot 82 in FIG. 6. In FIG. 6, one hand must be used to raise the stop or latch bracket using tab 86 while the other hand is used to raise the handle 74. With the bracket of FIG. 7, the latch can be unlocked and the handle raised with a single hand. A hand holding the bracket 74 could release the stop or latch bracket 80 by thumb on tab 86.

Figure 8:
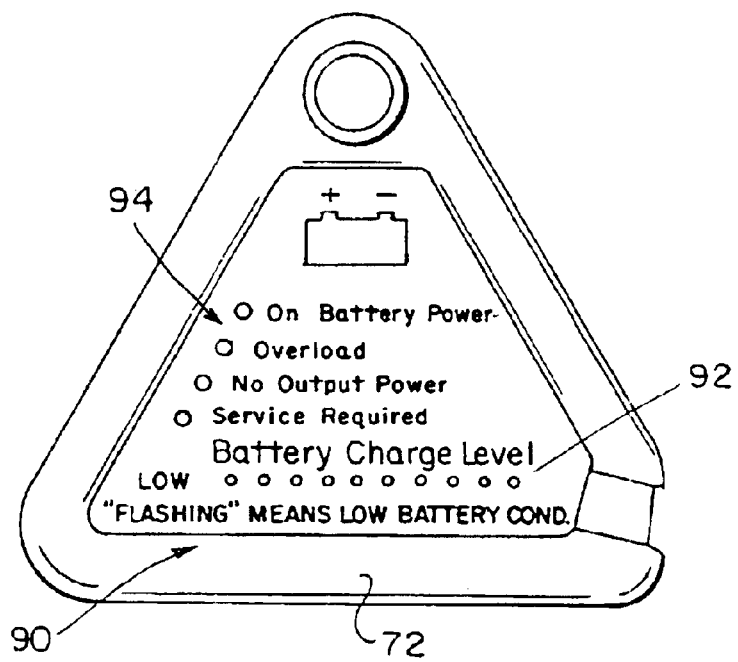
FIG. 8 is a plan view of a battery display.

Before power cord 50 of the care cart 24 is disconnected from outlets 18, the caregiver must check to determine whether the on-board battery 52 and the gas supply on care cart 24 are in proper working order. A power display panel 90 shown in FIG. 8 is on one of the lands 72 at the top of the care cart 24. Power display 90 provides information on the charge status and condition of the on board battery 52 when the battery 52 is both plugged into the room and when discharging during transport. The display 90 illustratively includes two separate display sections. The first display section 92 provides a display of battery charge level. The second display section includes status indicator 94.

The first display 92 is a series of indicators which form a bar graft of the battery charge level. Each position may have a different shade or brightness. The display 92 may flash when the battery charge is low.

The operating status is indicated by indicators 94 which may be LED, an LCD or other display. An indicator 94 is only illuminated when a particular condition exists. Illustratively, the status conditions include lighting an indicator when a battery power is on. Lighting an indicator when no input power is detected or there is an overload. An indicator is lit when service is required. An audible alarm can also be provided.

Figure 9:
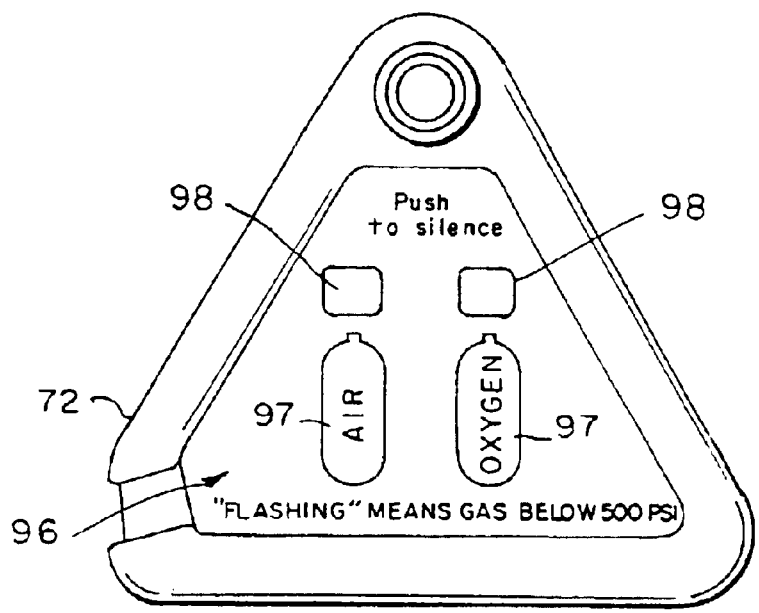
FIG. 9 is a plan view of a gas display.

The other land 72 includes a fluid supply indicator 96 as shown in FIG. 9. By way of example, an indicator 97 is shown for air and oxygen. If the indicator flashes, the gas supply is below a predetermined level, for example 500 PSI. An audible alarm may also be provided. Touch pads 98 are provided to silence the alarm.

Figure 10:
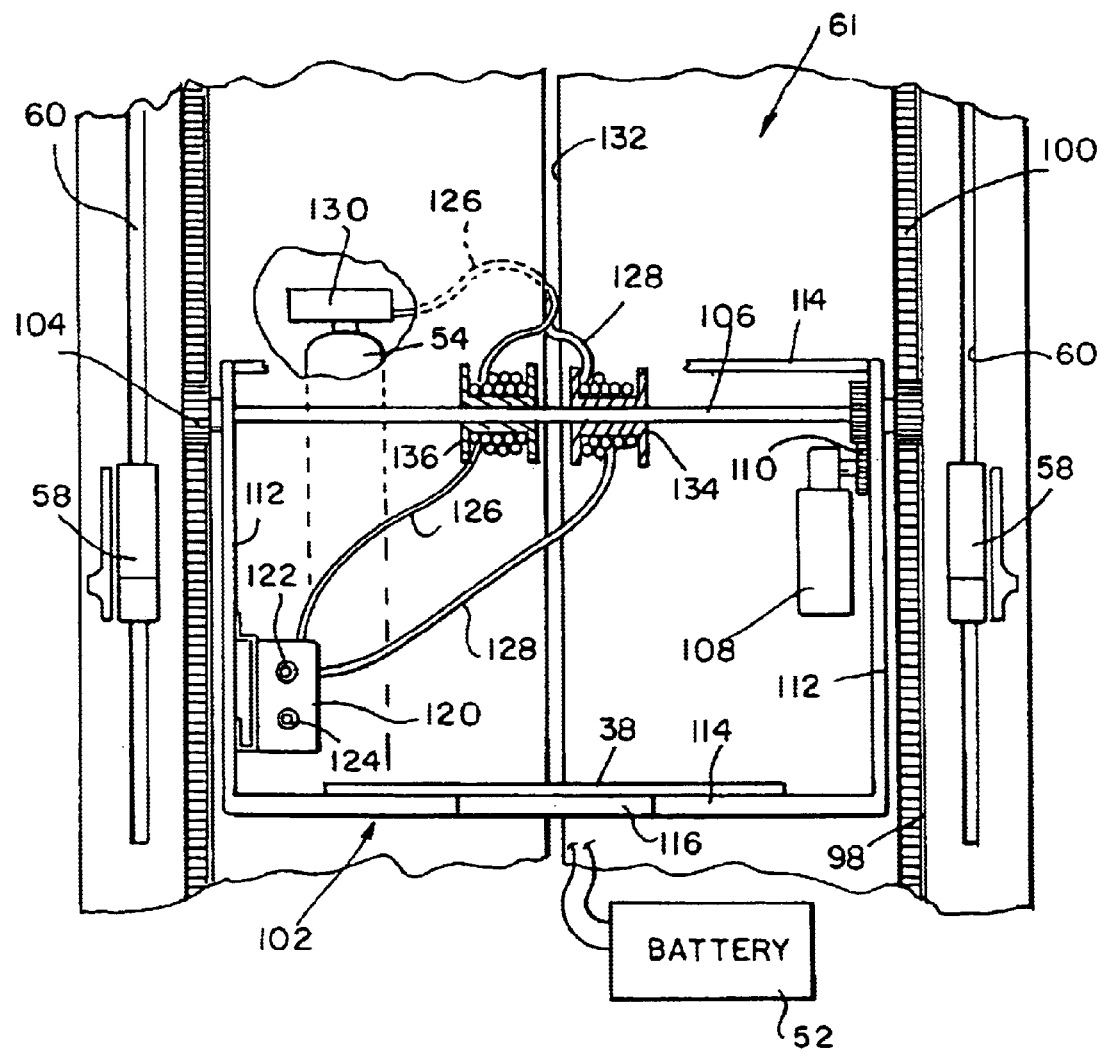
FIG. 10 is a schematic of the connection of the ports and line connecting accessories on the movable support and equipment shelf to sources on the cart according to the principles of the present invention.

As illustrated in FIGS. 2 and 10, an internal rack 100 having a plurality of teeth are exposed in slot 98 of front face 61 of the care cart. A movable support 102 which carries the equipment shelf 38 is coupled to the care cart. Gears 104 in the movable support 102 cooperates with each of the racks 100. A shaft 106 extends between the gears 104. A motor 108 and gearbox 110 on the movable support 102 are used to rotate shaft 106 and to move the support 102 up and down to control the height of shelf 38. A control switch 114 shown in FIG. 4 is adjacent a top end of the care cart 24 and controls motor 108 to move the support upwardly and downwardly.

Referring to FIG. 7, the movable support 102 includes a pair of sides 112 to which is mounted the shaft 106, motor 108 and gear box 110. A pair of braces 114 along the top and bottom are secured to the sides 112. The sides 112 extend into the openings 98 in the face 61 of the cart and have a flange, not shown, along the back of the front face of the cart. This limits the horizontal movement of the movable support 102 while allowing vertical movement. A support arm 116 extends from the lower brace 114. The equipment shelf 38 is pivotally connected to the support arm 116.

Figure 3:
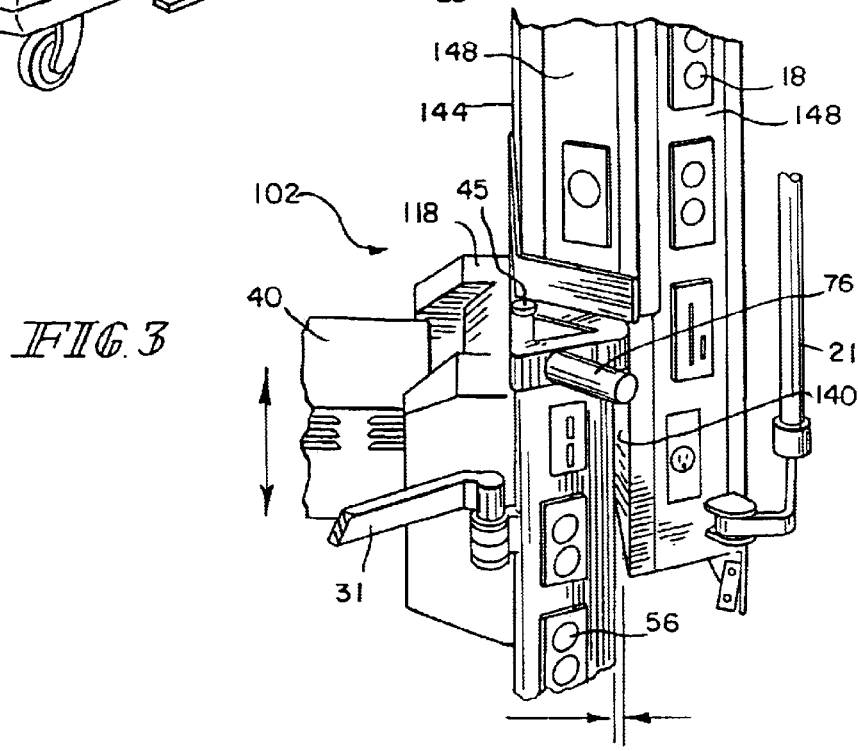
FIG. 3 is a partial perspective view of the nesting of the mobile care cart to the pivotal power column.

It should be noted in FIG. 10 that the cover 118 for the movable support 102 has been removed. As can be seen in FIGS. 2, 3 and 13, the cover 118 is generally U-shaped and receives support arm 116 of the equipment shelf 38 therebetween. One leg of the U-shaped cover 118 receives the motor 108, gear box 110 and one of the gears 104. The other leg of the U of cover 118 includes the other gear 104 and a terminal 120 having a pair of ports 122 and 124 therein as illustrated in FIG. 10. Lines 126 and 128 are connected to port 122 and 124 respectively and are contained within the interior of the cover 118. The ports 122 and 124 are for life support equipment, for example, ventilator 40, on equipment shelf 38. Thus, the lines, be they electrical cords or fluid tubes of the equipment on the shelf are plugged into the ports 122 and 124 and move with the shelf. The ports may also be data or communication ports. The connection of the ports 122 and 124 to their sources, be it a gas source or an electrical source, is through the interior of the housing 118 of the movable support 102. This reduces the entanglement of the support lines for the equipment on the equipment shelf 38.

The line 126 is shown connected to a manifold 130 on the back side of the cart which is connected to tank 54. The other line 128 may be connected to a different manifold and tank. For example, terminal 122 may provide oxygen and terminal 124 may provide hospital air. Lines 126 and 128 connected to ports 122 and 124 extend through slot 132 in the front face 61 of the cart. Although not shown, the electrical connections to the motor 108 would also extend through slot 132 in the face 61. As an alternative, the lines 126 and 128 for the ports and the lines for the motor may extend through slots in the face 61 adjacent a respective edge of the face 61.

If the length of lines 126 or 128 is relatively short with respect to its connection to its source, they may be connected directly to their source through the slot 132. If the source of one of the lines is far from the cart, or the amount of movement of the shelf 38 is of concern, take up reels 134 and 136 may be provided for the lines 126 and 128. The take up reels are connected to shaft 106 and are driven by the shaft to change the length of the line with the movement of the support equipment shelf 38. Thus, the reels 134 and 136 would play-out or lengthen the lines 126, 128 in one direction of rotation and shorten or reel-in the lines 126 and 128 in the opposite direction of rotation of shaft 106.

The placement of reels 134 and 136 may be any place along the shaft 106. If they are extremely thick, they would be place in the legs of the L of the cover 118. If they are placed closer to the edge, a pair of slits 132 may be provided adjacent the sides of the movable support 102.

The locator portion 16 of the power column 10 includes a front face 140 and bottom face 142 of the body 14 of the power column 10 as illustrated in FIG. 1. The front portion of body 14 includes a front face 144 and a pair of front portion side faces 146. The rear portion of the power column 10 extends the length of the body portion 14 and the locator 16 and includes side faces 148 and a rear face 150, generally parallel to the front face 140 and 144.

When the care cart 24 is nested with the power column 10, as illustrated in FIGS. 2 and 3, the bottom face 142 of the locator is received in the recess 70 in the top of the care cart 24 between lands 72. The back of the care cart 24 is adjacent to the front face 140 of the locator 16. The combined mobile cart and power column form a complete power column unit and constitute the lower and upper sections respectively, thereof.

The fit between the power column 10 and the cart 24 may be a loose fit, in which case, the combination are moved rearwardly by moving the cart 24 rearwardly or moving it forwardly by moving the column 10 forward. The side handle 76 of the cart aid moving the combination rearwardly. As an alternative, the fit between the power column 10 and the cart 24 at locator 16 may be a friction fit. The handle 74 in the stored position may engage the bottom face 142 and aid in achieving such a friction fit. When the care cart 24 is latched coupled to a bed, the movement of the bed with the latched cart is sufficient to overcome the friction fit.

As illustrated, the land 72 are substantially triangular forming a trapezoidal recess 70. The front face 144 and side faces 146 of the front portion of the body 14 of the power column also have a trapezoidal cross section which is to be received in the trapezoidal recess 70. It should also be noted that the back face 150 and the side faces 148 of the rear portion of the power column 10 also forms a trapezoidal cross section. The particular selections of the cross sections are purely aesthetic and any cross section may be used. Preferably, the cross section of the front face 144 and side faces 146 will be complementary to the cross-section of the recess 70 to provide proper nesting.

Figure 11:
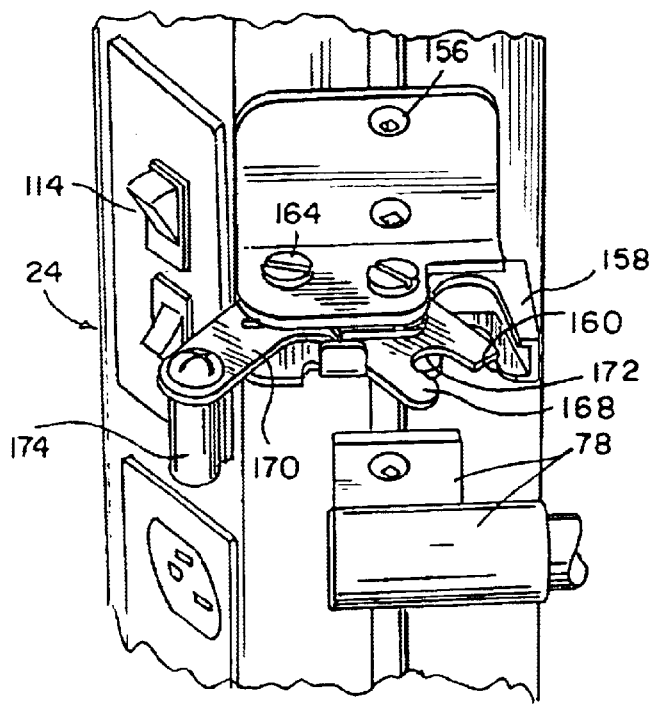
FIG. 11 is a perspective view of a latch connecting the care cart to the power column in its open position according to the principles of the present invention.
Figure 12:
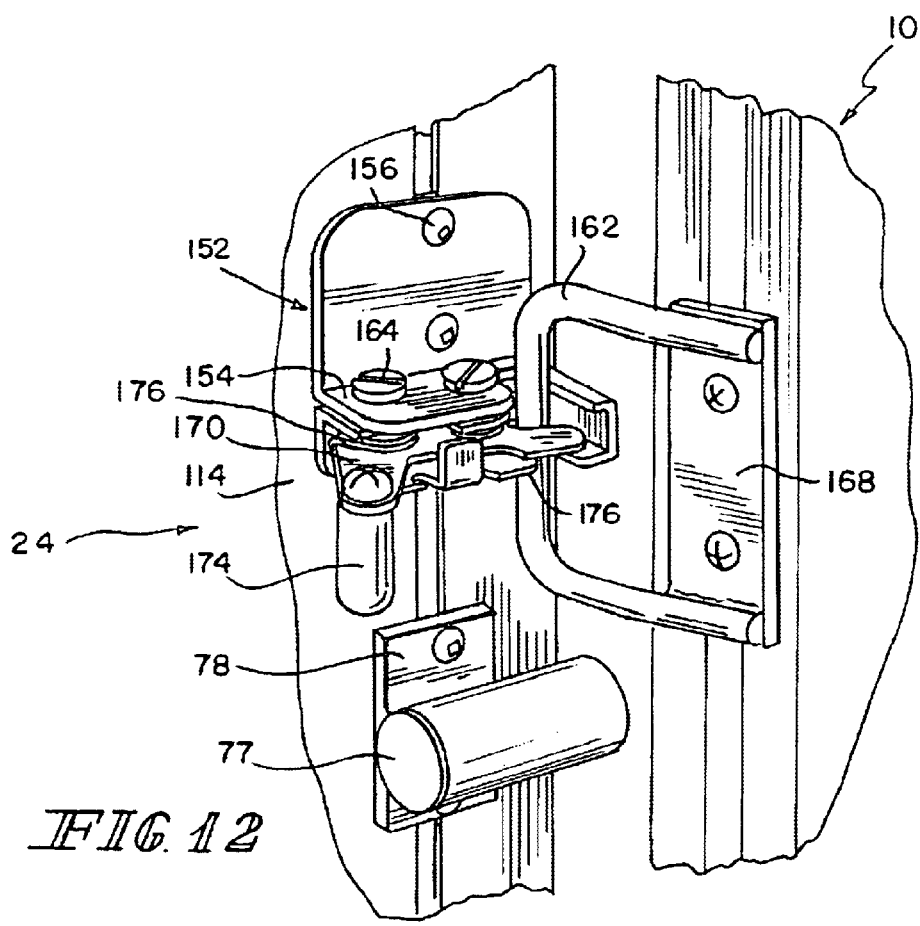
FIG. 12 is a perspective view of the latch of FIG. 11 in its closed position.

As an alternative, a latch may be provided to secure the cart 24 to the power column 10. Such a latch is illustrated in FIGS. 11 and 12. A latch 152 includes a bracket mounted to the cart by fasteners 156. The position illustrated in FIGS. 11 and 12 is above the bracket 78 of the handle 74. A housing 158 includes a U-shaped channel 160 to receive a post 162. The housing 158 is mounted to the bracket 154 by fasteners 164 and the post 162 is mounted to the power column 10 by fasteners 166. The latch 152 includes two links 168 and 170 which are cam to be bistable or an over center linkage in housing 158. The cam 168 includes a U-shaped recess 172 to receive the post 162 and the link 170 includes a handle 174. A pair of coil springs 176 connected to each of the links 168 and 170 bias the cams to the open position illustrated in FIG. 11.

When the post 162 intersects the recess 172 in link 168, it rotates the link 168 counter clockwise into the housing and allowing the post 162 to be guided into recess 160 of the housing 158. This force overcomes the force of the springs 176 and causes the links 170 and 168 to become unstable and snap into the closed position illustrated in FIG. 12. To release the latch, the handle 178 is moved to rotate the link 170 in a counter-clockwise direction thereby driving the link 168 in the clockwise direction. This releases the post 162. The general operation of this mechanism is very similar to the safety door locks on automobiles.

It should also be noted that a similar structure to latch 152 can be used in lieu of the latch 58 which latches the care cart 24 to the bed 25.

FIG. 13 is a general overview of a bed 25, care cart 24 and power column 10 in a transition state. The cart 24 is disconnected from the power column and is being prepared to be attached to the bed. The bed is raised and the equipment shelf 38 is lowered. The power and fluid lines are disconnected from the power column 10 and a transport monitor 42 is mounted on the cart. Subsequently, the care cart 24 is latched to the bed 25. FIG. 13 illustrates two power cords, one for the battery 48 and one for general power 50.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. A mobile care cart comprising:
 a base having side walls and an upwardly-facing top wall;
 patient treating accessories on the base;
 a recess in the upwardly-facing top wall of the base;
 a U-shaped handle having a central portion and a pair of leg portions extending from the ends of the central portion, the pair of leg portions being pivotally coupled to the side walls of the base to pivot the U-shaped handle between a raised stored position in which the central portion lies in the recess in the upwardly-facing top wall and an extended lowered position in which the central portion lies outside the recess in the upwardly-facing top wall.

2. The mobile care cart of claim 1, wherein the central portion and the leg portions of the U-shaped handle are generally in a plane; the handle further includes extensions extending from the ends of the leg portions and transverse to the plane defined by the central portion and the leg portions; and the extensions pivotally mount the handle to the base.

3. The mobile care cart of claim 1, including a stop connecting the handle to the base and limiting the extended lowered position.

4. The mobile care cart of claim 3, wherein the stop includes a bracket having a first elongated slot and a pin riding in the slot.

5. The mobile care cart of claim 4, wherein the bracket includes a second slot extending transverse to the first slot and in which the pin rides to latch the handle in the extended lowered position.

6. The mobile care cart of claim 1, including a latch which latches the handle to the base in the extended lowered position.

7. The mobile care cart of claim 6, wherein the latch includes a bracket having a first elongated slot and a second slot extending transverse to the first slot, and a pin riding in the slots to latch the handle in the extended lowered position when the pin is in the second slot.

8. A mobile care cart apparatus comprising:
 a base;
 two legs, each leg having a first end pivotally mounted to the base;
 two wheels, each wheel being mounted to a respective second end of the legs;

the legs pivoting the wheels from a respective first position to a respective second position, the wheels being closer to each other in the respective first positions than in the respective second positions; and a driver coupled to the legs and including springs biasing the legs to the respective first positions.

9. The apparatus of claim 8, wherein the driver includes linkages connecting the springs and legs.

10. The apparatus of claim 8, wherein each leg includes a shaft pivotally mounted to the base and the driver is coupled to the shafts, the base includes a housing, and the driver is in the housing.

11. The apparatus of claim 10, including a first latch for coupling the apparatus to a hospital bed and patient treating accessories on the apparatus.

12. The apparatus of claim 8, wherein the pair of legs are back legs pivotally mounted adjacent a back of the base at the first ends of the back legs and having a wheel mounted at the second ends of the back legs, a driver for each of the back legs, and including a pair of front legs mounted adjacent a front of the base at first ends of the front legs and having a wheel mounted at second ends of the front legs.

13. The apparatus of claim 8, wherein the first position extends backwards from the back of the base and the second position is substantially coplanar with the back of the base.

14. A patient treating apparatus in combination with a bed and a hospital room comprising:

a power column having electrical outlets, fluid ports and patient treating accessories;

the power column having an upper section and a separable lower section;

an arm pivotally mounting the upper section to the room;

the lower section including a movable base with wheels; and electrical outlets, fluid ports and patient treating accessories on both the upper and lower sections;

the lower section moving with the upper section independent of the bed when the separable lower section is decoupled from the bed and coupled to the upper section, the lower section providing patient treatment when the separable lower section is decoupled from the upper section and coupled to the bed, and the bed and the lower section are separated from the upper section and moved relative thereto.

15. The apparatus of claim 14, wherein the upper section includes a recess in which at least a portion of the separable lower section nests.

16. The apparatus of claim 14, wherein the separable lower section includes a latch for coupling the separable lower section to the hospital bed, and the separable lower section moves with the upper section independent of the bed when the latch does not couple the separable lower section to the bed.

17. The apparatus of claim 14, wherein the electrical outlets and fluid ports on the upper section are connected to sources in the room, and the electrical outlets and fluid ports on the separable lower section are connected to sources on the base.

18. The apparatus of claim 14, including a latch connecting the separable upper and lower sections.

19. The apparatus of claim 18, wherein the latch includes an over center locking linkage.

20. The apparatus of claim 14, wherein the separable upper and lower sections are configured to nest together.

21. The apparatus of claim 20, wherein the separable lower section includes a latch for coupling the separable lower section to the hospital bed, and the upper and lower sections separate when the separable lower section is coupled by the latch to the bed and moves with the bed relative to the upper section.

22. The apparatus of claim 14, wherein the separable lower section includes a recess in which a portion of the upper section nests.

23. The apparatus of claim 14, wherein a lower portion of the upper section is formed with at least one recess and at least one detent and an upper portion of the separable lower section is formed with at least one recess and at least one detent so that the separable upper and lower sections removably nest with one another when the upper and lower sections are brought together.

24. A mobile care cart having a base with wheels, a source on the base, a rigid support movably coupled to the base for movement between an elevated position and a lowered position, and patient treating accessories; and wherein at least one patient treating accessory is located on the movable support, the movable support includes a port configured to be connected to the at least one patient treating accessory located thereon and movable therewith relative to the source on the base, and a line connecting the port on the movable support to the source on the base.

25. The mobile care cart of claim 24, including a take-up spool on the base and engaging the line to automatically change length of the line with movement of the support.

26. The mobile care cart of claim 25, including a drive coupling the movement of the support to the spool.

27. The mobile care cart of claim 24, including a take-up spool on the support and engaging the line to automatically change length of the line with movement of the support.

28. The mobile care cart of claim 27, including a drive coupling the movement of the support to the spool.

29. The mobile care cart of claim 24, wherein the source is a battery, and the line is an electrical cord connected to the battery on the base.

30. The mobile care cart of claim 24, wherein the source is a fluid source, and the line is a tube connected to the fluid source on the base.

31. A mobile care cart comprising:

a base;

patient treating accessories on the cart;

a handle pivotally coupled to the cart to pivot between a raised stored position and a lowered extended position; and a bracket and a pin connected between the cart and the handle, the bracket having a first elongated slot and a second slot extending transverse to the first slot, the pin riding in the first slot as the handle pivots between the raised stored position and the lowered extended position, and the pin latching the handle in the lowered extended position when the pin is in the second slot.

32. The mobile care cart of claim 31, wherein the latch includes a tab extending from the bracket to facilitate lifting of the bracket to move the pin from the second slot to the first slot for releasing the latch.

* * * * *